US007037260B2

(12) United States Patent
Keirsbilck et al.

(10) Patent No.: US 7,037,260 B2
(45) Date of Patent: *May 2, 2006

(54) METHOD AND APPARATUS FOR DETERMINING ATTENTION DEFICIT HYPERACTIVITY DISORDER (ADHD) MEDICATION DOSAGE AND FOR MONITORING THE EFFECTS OF ADHD MEDICATION ON PEOPLE WHO HAVE ADHD USING COMPLEMENTARY TESTS

(75) Inventors: Richard S. Keirsbilck, Rochester, NY (US); Peter A. Parks, Topeka, KS (US); David L. Patton, Webster, NY (US); Richard N. Blazey, Penfield, NY (US); Paige Miller, Rochester, NY (US)

(73) Assignee: McLean Hospital Corporation, Belmont, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/832,824

(22) Filed: Apr. 27, 2004

(65) Prior Publication Data

US 2005/0025704 A1 Feb. 3, 2005

Related U.S. Application Data

(63) Continuation of application No. 10/092,284, filed on Mar. 6, 2002, now Pat. No. 6,726,624.

(51) Int. Cl.
*A61B 5/00* (2006.01)

(52) U.S. Cl. ..................................... 600/300; 600/549

(58) Field of Classification Search ........ 600/300–301, 600/483, 547–549, 558, 544–545; 128/905, 128/820, 897, 828; 424/239.1, 408, 449
See application file for complete search history.

(56) References Cited

U.S. PATENT DOCUMENTS

| 5,199,439 | A | * | 4/1993 | Zimmerman et al. | ........ 600/483 |
| 5,630,664 | A | * | 5/1997 | Farrelly | ........................ 600/508 |
| 5,720,773 | A | * | 2/1998 | Lopez-Claros | ................ 607/96 |
| 6,255,325 | B1 | * | 7/2001 | Dariani et al. | ............... 514/317 |
| 6,325,763 | B1 | * | 12/2001 | Pfeiffer et al. | .............. 600/549 |
| 6,375,622 | B1 | * | 4/2002 | Kao et al. | .................... 600/485 |
| 6,520,921 | B1 | * | 2/2003 | Patton et al. | ................ 600/549 |
| 6,726,624 | B1 | * | 4/2004 | Keirsbilck et al. | ........... 600/300 |

* cited by examiner

*Primary Examiner*—Max F. Hindenburg
*Assistant Examiner*—Michael C. Astorino

(57) ABSTRACT

A method for determining the appropriate dosage of a medication to treat Attention Deficit Hyperactivity Disorder (ADHD) in an individual who has ADHD. The method comprises sampling the peripheral skin temperature of left and right like extremities of an individual during a predetermined time interval when the individual is in a sensory deprived state to provide respective left and right sampled peripheral skin temperature data, processing the sampled peripheral skin temperature data; processing the sampled peripheral skin temperature data including filtering, differentiation, and conversion to the frequency domain to derive spectral signatures whose magnitudes are indicative of the level of ADHD manifestation. The effectiveness of the medication is calculated by comparison to predetermined threshold values.

2 Claims, 10 Drawing Sheets

```
SAMPLE RATE (Hz):     32.000000
STOPBAND FREQ (Hz):    0.010000
PASSBAND RIPPLE (dB): 12.000000
STOPBAND ATTEN (dB): 72.000000
CUTOFF FREQ (Hz):      0.020000
FILTER ORDER:         32
``` fRATE/2 - SAMPLE RATE           Hz
fSTOP   - STOPBAND FREQUENCY    Hz
ATTN    - STOPBAND ATTENUATION  dB
fCUT    - CUTOFF FREQUENCY      Hz

0 < fSTOP < fCUT < fRATE/2

METHOD AND APPARATUS FOR DETERMINING ATTENTION DEFICIT HYPERACTIVITY DISORDER (ADHD) MEDICATION DOSAGE AND FOR MONITORING THE EFFECTS OF ADHD MEDICATION ON PEOPLE WHO HAVE ADHD USING COMPLEMENTARY TESTS

CROSS REFERENCE TO RELATED APPLICATIONS

This application is a continuation of and claims priority from U.S. Ser. No. 10/092,284, filed Mar. 6, 2002, now U.S. Pat. No. 6,726,624.

FIELD OF THE INVENTION

This invention relates in general to technique for monitoring the effectiveness of medication taken to treat Attention Deficit Hyperactivity Disorder (ADHD) and more particularly to a technique and apparatus for measuring and objectively analyzing an individual's peripheral temperature variability to determine values indicative of the level of manifestation of ADHD.

BACKGROUND OF THE INVENTION

ADHD is the most common neurobehavioral disorder of childhood as well as among the most prevalent health conditions affecting school-aged children. Between 4% and 12% of school age children (several millions) are affected. $3 billion is spent annually on behalf of students with ADHD. Moreover, in the general population, 9.2% of males and 2.9% of females are found to have behavior consistent with ADHD. Upwards of 10 million adults may be affected.

ADHD is presently a difficult disorder to diagnose. The core symptoms of ADHD in children include inattention, hyperactivity, and impulsivity. ADHD children may experience significant functional problems, such as school difficulties, academic underachievement, poor relationships with family and peers, and low self-esteem. Adults with ADHD often have a history of losing jobs, impulsive actions, substance abuse, and broken marriages. ADHD often goes undiagnosed if not caught at an early age and affects many adults who may not be aware of the condition. ADHD has many look-alike causes (family situations, motivations) and co-morbid conditions (depression, anxiety, and learning disabilities) are common.

Diagnosis of ADHD currently involves a process of elimination using written and verbal assessment instruments. However, there is no one objective, independently validated test for ADHD. Various objective techniques have been proposed but have not yet attained widespread acceptance. These include:

1. The eye problem called convergence insufficiency was found to be three times more common in children with ADHD than in other children by University of California, San Diego researchers.

2. Infrared tracking to measure difficult-to-detect movements of children during attention tests combined with functional MRI imaging of the brain were used by psychiatrists at McLean Hospital in Belmont, Mass. to diagnose ADHD in a small group of children (*Nature Medicine*, Vol. 6, No. 4, April 2000, Pages 470–473).

3. Techniques based on EEG biofeedback for the diagnoses and treatment of ADHD are described by Lubar (*Biofeedback and Self-Regulation*, Vol. 16, No. 3, 1991, Pages 201–225).

4. U.S. Pat. No. 6,097,980, issued Aug. 1, 2000, inventor Monastra et al, discloses a quantitative electroencephalographic process assessing ADHD.

5. U.S. Pat. No. 5,913,310, issued Jun. 22, 1999, inventor Brown, discloses a video game for the diagnosis and treatment of ADHD.

6. U.S. Pat. No. 5,918,603, issued Jul. 6, 1999, inventor Brown, discloses a video game for the diagnosis and treatment of ADHD.

7. U.S. Pat. No. 5,940,801, issued Aug. 17, 1999, inventor Brown, discloses a microprocessor such as a video game for the diagnosis and treatment of ADHD.

8. U.S. Pat. No. 5,377,100, issued Dec. 27, 1994, inventors Pope et al., discloses a method of using a video game coupled with brain wave detection to treat patients with ADHD.

9. Dr. Albert Rizzo of the integrated Media Systems Center of the University of Southern California has used Virtual Reality techniques for the detection and treatment of ADHD.

10. U.S. Pat. No. 6,053,739, inventors Stewart et al., discloses a method of using a visual display, colored visual word targets and colored visual response targets to administer an attention performance test.

U.S. Pat. No. 5,377,100, issued Dec. 27, 1994, inventors Patton et al., discloses a system and for managing the psychological state of an individual using images.

U.S. Pat. No. 6,117,075 Barnea discloses a method of measuring the depth of anesthesia by detecting the suppression of peripheral temperature variability.

There are several clinical biofeedback and physiologic monitoring systems (e.g. Multi Trace, Bio Integrator). These systems are used by professional clinicians. Although skin temperature spectral characteristics have been shown to indicate stress-related changes of peripheral vasomotor activity in normal subjects, there has been no disclosure of use of variations in skin-temperature response to assist in diagnosing ADHD. (See: Biofeedback and Self-Regulation, Vol. 20, No. 4, 1995).

As stated above, the primary method for diagnosing ADHD is the use of a bank of written and verbal assessment instruments designed to assess the children for behavioral indicators of criteria established by American Medical Association (AMA) as described in the Diagnostic and Statistics manual—IV (DSM-IV). Psychiatrists, psychologists, school psychologists and other licensed practitioners administer these assessment instruments. In some cases those individuals who meet DSM-IV criteria for ADHD diagnosis are prescribed a drug such as Ritalin. Behavioral observations of the patient while on Ritalin are conducted to assess the impact of prescribed medication. However, clearly established criteria for evaluating the impact of specific medications e.g., Ritalin and specific dosages are lacking. It would be advantageous for physicians to have access to clearly established physiologic criteria, which could be measured, to determine if a specific medication at a specific dosage effectively addressed the underlying physiologic parameter, which was indicative of ADHD.

There is thus a need for a simple, inexpensive, and reliable objective technique for determining the effectiveness of the medication and appropriate dosage taken to counteract ADHD by an individual who has ADHD.

SUMMARY OF THE INVENTION

According to the present invention, there is provided a solution to the problems discussed above.

According to a feature of the present invention, there is provided a method for determining the appropriate dosage of a medication to treat Attention Deficit Hyperactivity Disorder (ADHD) in an individual who has ADHD comprising:

(a) sampling the peripheral skin temperature of left and right like extremities of an individual during a predetermined time interval when the subject is in a sensory deprived state to provide respective left and right sampled peripheral skin temperature data;

(b) a first processing of at least one of said left and right sampled peripheral skin temperature data providing conversion to the frequency domain to derive a first spectral signature having magnitude values;

(c) a second processing of both said left and right sampled peripheral skin temperature data to derive temporally correlated differential data;

(d) said second processing further filtering said differential data with a high pass filter to produce filtered differential data with near d, c, components removed;

(e) said second processing lastly providing conversion to the frequency domain of said filtered differential data to derive a second spectral signature having magnitude values;

(f) a third processing of the said first spectral signature for the determination of the level of manifestation of ADHD by comparison to a predetermined first threshold value;

(g) a fourth processing of the said second spectral signature for the determination of the level of manifestation of ADHD by comparison to a predetermined threshold value; and (h) a fifth processing wherein an assessment of the bi-modal quality of the results of the third and fourth processing is made, to provide a final determination of one of the following three possibilities:
(i) a various level of dosage change;
(ii) dosage level is adequate,
(iii) there is noise in the data.

ADVANTAGEOUS EFFECT OF THE INVENTION

The invention has the following advantages.
1. A device and technique for objectively determining the effectiveness of the medication and appropriate dosage taken to counteract ADHD by an individual who has ADHD which is simple, inexpensive and reliable.

DETAILED DESCRIPTION OF THE INVENTION

According to the present invention, it has been found that signatures of ADHD are hidden in fluctuation of the temperature of the skin as measured at the extremities such as at the fingertips. In general, as an individual's stress level increases the peripheral vasculature constricts and often the person's blood pressure increases. As the blood vessels in the body constrict, blood flow is restricted. This is most easily monitored in the extremities such as the fingers, because the blood vessels in the extremities are small and very responsive to Sympathetic Nervous System (SNS) innervations. A direct result of decreased blood flow to the blood vessels in the extremities is a decrease in the peripheral temperature of the extremities. Conversely, as an individual's stress level decreases and relaxation occurs, the blood vessels expand, allowing blood to flow in a less restricted manner. As the blood flow to the vessels in the extremities increases the peripheral temperature of the extremities increases. It is suspected that when a subject with ADHD is subjected to sensory deprivation such as being made to look at a blank screen or an obscured image for a period of time in an inactive state, the lack of stimulation increases and there tends to be a shift in the subject's physiologic reactivity indicative of an increase in their stress level. As their stress level increases their blood vessels contract and the peripheral temperature of their extremities decreases. Biofeedback practitioners have long used measurement of hand temperature to help subjects manage their physiology by controlling blood flow to the extremities. The literature reports that reduced blood flow to the brain is frequently found in patients with ADHD.

In addition to peripheral skin temperature and peripheral skin temperature variability there are other known physiologic measures which are known (or potential) indicators of stress such as; bilateral temperature variability, heart rate, heart rate variability, muscle tension (excessive and chronic, measured via surface electromyography—sEMG), bilateral muscle tension imbalance, galvanic skin response (i.e. electro dermal response—EDR), eye saccades, blood oxygen ($SpO_2$), salivary IGA, electroencephalography (EEG), peripheral blood flow (measured via photoplethismography—PPG), and peripheral blood flow variability (PPG).

Figure 1:
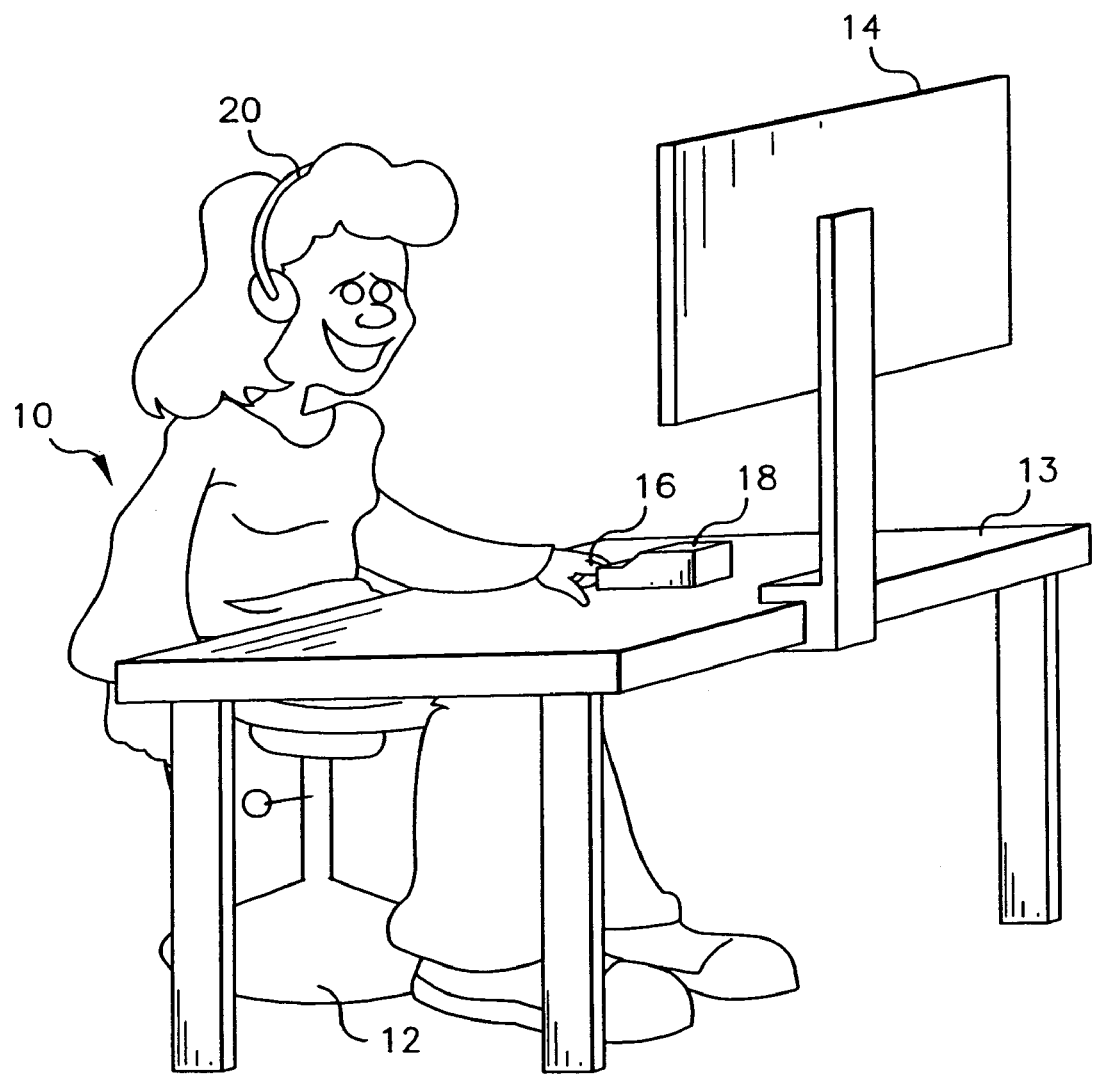
FIG. 1 is a diagrammatic view illustrating use of an embodiment of the present invention.

As shown in FIG. 1, a subject 10 is sitting on a chair 12 at a table 13 watching a screen 14. The screen 14 is used to block any visual stimulus from disturbing the subject 10. Since said visual stimulus may be in the subject's peripheral vision, the screen 14 illustrated in FIG. 1 may be larger, for example a blank wall or corner of a room. In another embodiment, which is not shown, the subject can wear a pair of translucent glasses, goggles or eye mask for the same purpose. These devices may be internally illuminated for uniformity and to further minimize the propensity to self-stimulate with mental images, which is easier to do with a dark state before one's eyes. For the same reason, the subject is instructed to not close their eyes, except to blink. The subject 10 is wearing a set of headphones 20. The headphones 20 can be connected to a sound-generating device not shown. The headphones 20 can be used to block out ambient noise or to produce a white noise intended to reduce or eliminate the audio stimulus from the environment during the test. The subject is at rest in an inactive state and sensory deprived. The fingertip 16 of subject 10 is inserted into a temperature recording module 18 along groove 17, where the skin temperature is measured via a sensor 22 (shown in FIG. 2). A second temperature sensor module 28 is connected to the temperature recording module 18 via a cable 29. The second temperature sensor module 28 is used to sample the skin temperature of the subject's 10 other hand's fingertip and includes groove 34 and temperature sensor 36. In another embodiment of the present invention, to prevent the possibility of sensor to skin contact variability due to finger movement in the grooves 17; 34 and against the sensors 22; 36, the groove 17 corresponding sensor 22, and the second temperature sensor module 28 are replaced with discrete temperature sensors, both wired to the temperature recording module, and held in place against their respective fingertips by tape, or any such available means. The sensor glove disclosed in U.S. patent application Ser. No. 09/892,824, filed on Jun. 27, 2001, may also be preferably used.

Figure 2:
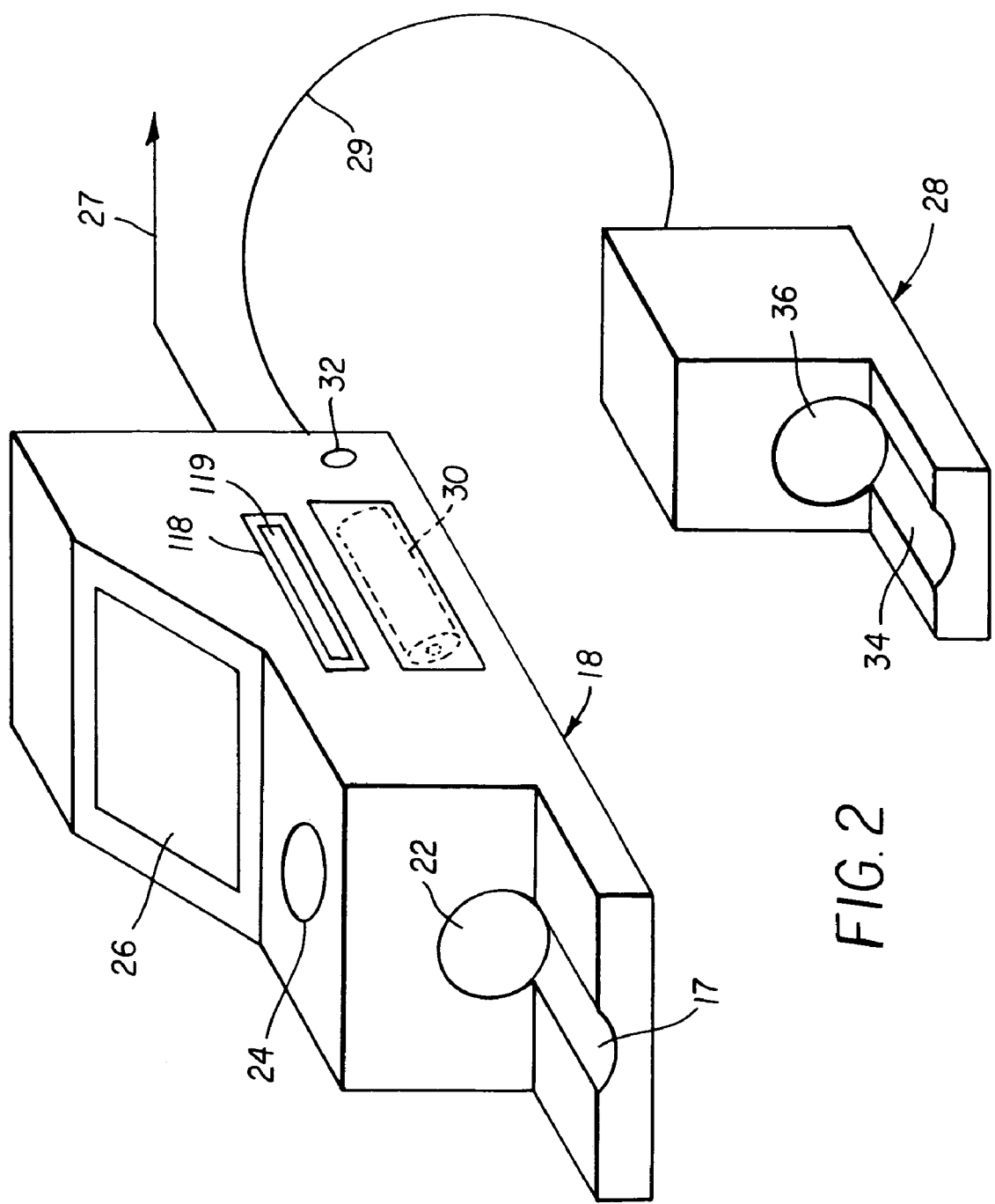
FIG. 2 is a perspective view showing in greater detail the embodiment of FIG. 1.

As shown in FIG. 2, the temperature recording module 18 also includes an on/off switch 24, and a display 26, which is disabled during a session The temperature recording module 18 can have an internal power supply, such as a battery 30, or an external low voltage power supply port 32 for an external low voltage power supply (not shown), such as used for a telephone. The temperature recording module 18 can be connected to an external data processor (not shown) via a cable 27 (such as a USB or RS 232 cable), optical fiber, or wireless transmitting device such as an RF or IR link (not shown).

In a further embodiment, a slot 118 is provided to accept a memory card 119 to allow the transport of the recorded temperature data. In these embodiments, the data processing and analysis is done at a different location, for example at a computer, a PDA device, or through the Internet. In another embodiment, the electronics to do the data processing and analysis is contained in the temperature recording module, with the results transported by any of the aforesaid means. The display 26 may also show the result, in addition to indicating that fingertip temperatures are being sensed correctly prior to the start of a session. In this self-contained configuration, the system may be made upgradeable by providing bi-directionality across the data transport path.

Figure 3A:
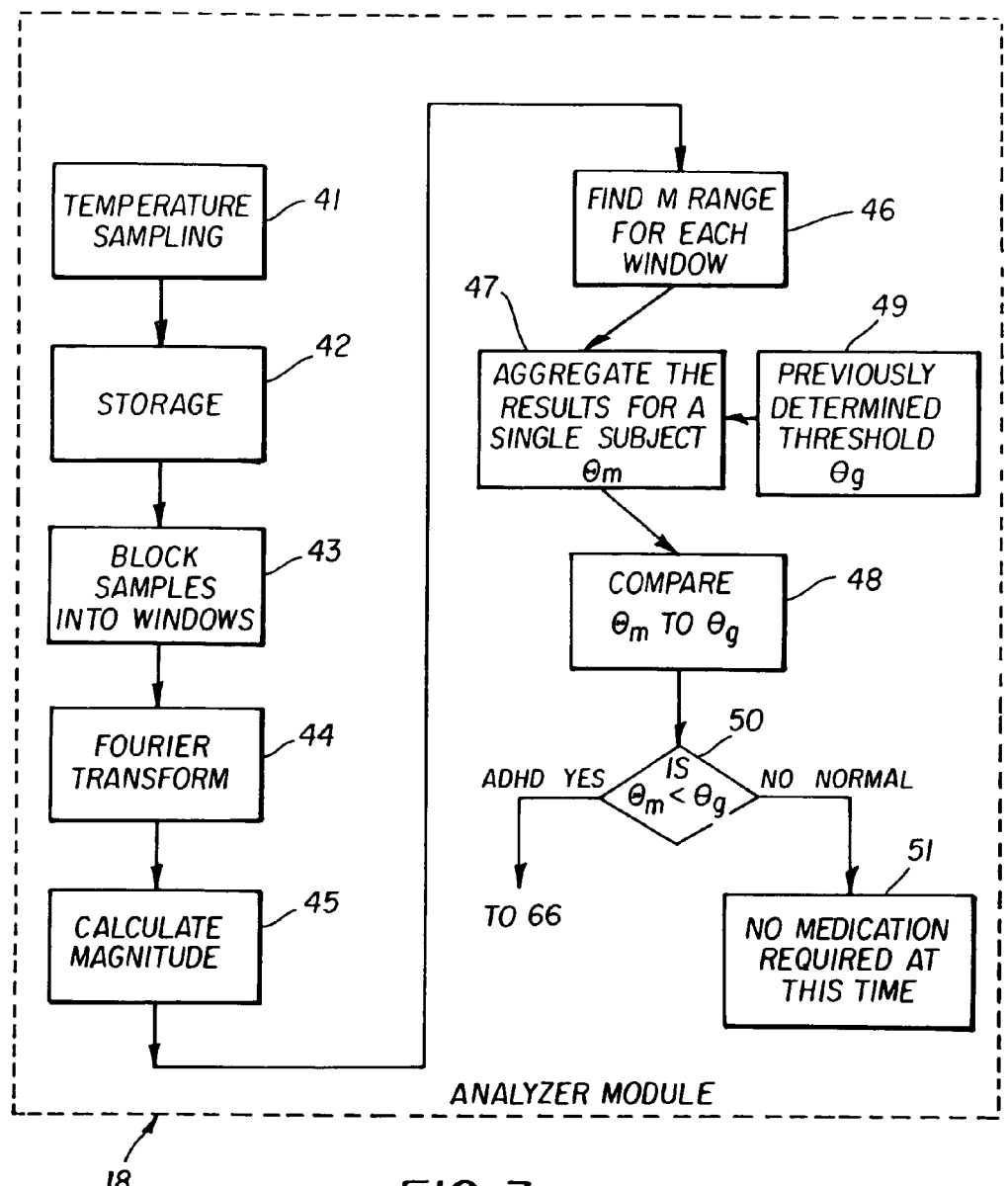
FIGS. 3a and 3b are block diagrams of portions of a system incorporating the present invention.

In FIG. 1, the fingertip temperatures are being recorded during an interval when the subject 10 has been asked to sit quietly for a period of about 10 minutes. Not shown is the recording sensor for the other fingertip. Fig. w shows an embodiment for recording said other fingertip. As shown in FIG. 3a, the temperature data is sampled by 41 at a time interval that provides 32 samples per second per sensor, creating at least two sets, left and right, of $_n$ temperature data, which are stored in storage 42.

First Processing

In the preferred embodiment of the present invention, a first processing is next carried out on these data. As shown in FIG. 3a, this processing begins with window blocking 43, continuing Fourier transform 44, Magnitude calculation 45, Mrange calculation 46, aggregation step block 47, Threshold comparison step block 48, previously determined threshold $\theta_g$ 49, and threshold comparison result block 50. The method of determining dosage is further expanded in FIG. 3b.

Now further referring to FIG. 3a, in block 43, the n samples are divided into z windows of m samples, each group corresponding to a given time window of width Δt (~32–64 sec) equally spaced in time (~50 sec) across the entire baseline data collection time 600 seconds. The data from each window is then passed through a Fast Fourier Transform (FFT) algorithm 44 producing $2^{m-1}$ data points spaced equally in frequency space for each window. The values are complex numbers having form $$FFT(f_m) = A(f_m) + B(f_m)i$$

where i is the $\sqrt{-1}$. The Phase $\Phi(f_m)$ is then found from the equation $$\Phi_l(f_m) = \tan^{-1}\left(\frac{B(f_m)}{A(f_m)}\right) \quad (1.0)$$

and the Magnitude $M(f_m)$ from $$M_l(f_m) = \sqrt{B(f_m)^2 + A(f_m)^2} \quad (1.1)$$

Figure 4:
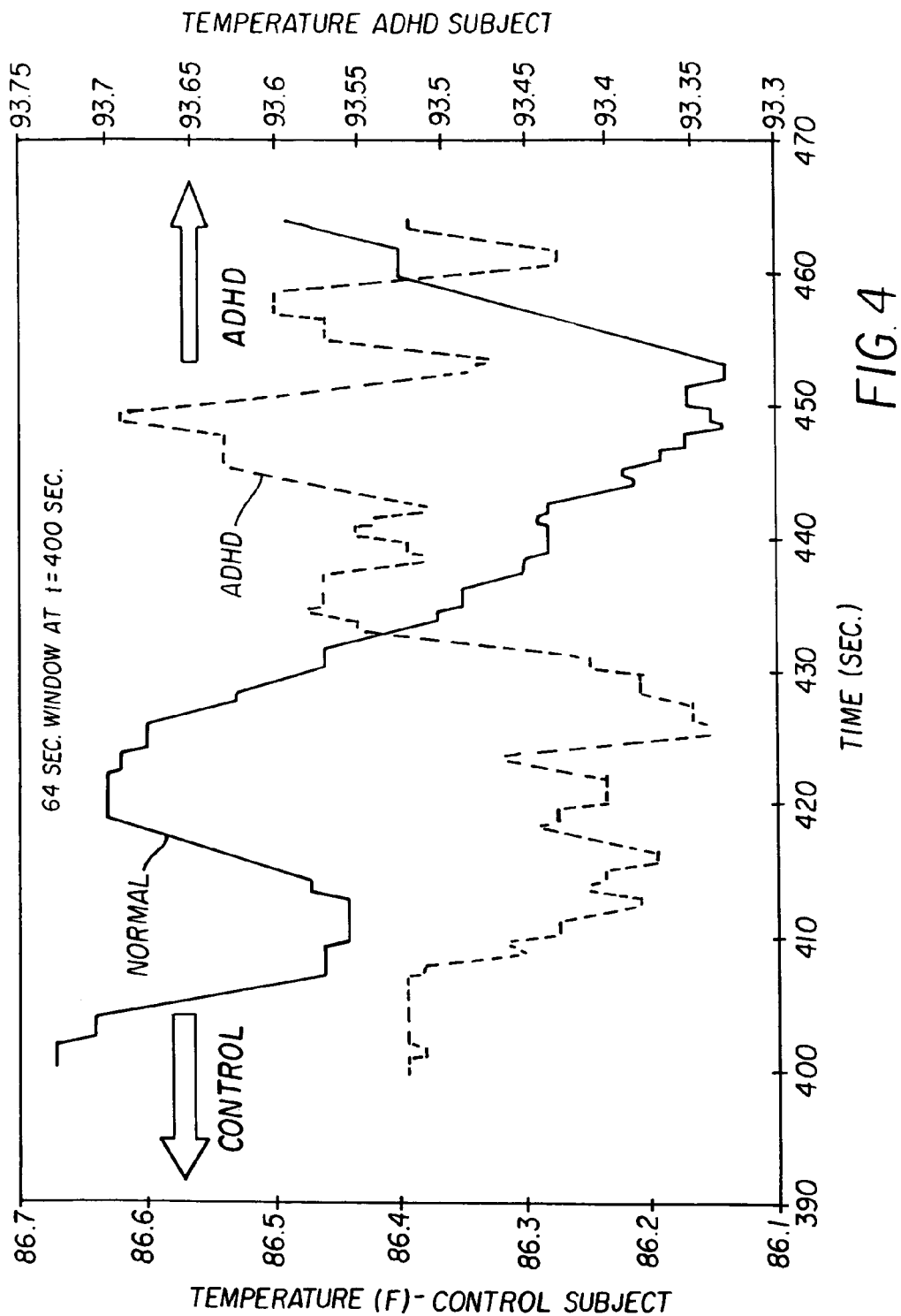
FIGS. 4, 5 and 6 are graphical views useful in explaining the present invention.

In the equations 1.0 and 1.1 the subscript l refers to the fact that a separate signal is extracted for each hand so the subscript is l for data extracted from the left-hand data and r for data from the right hand. FIG. 4 graphically illustrates the temperature signal during one window for a normal subject and a person diagnosed with ADHD.

Figure 5:
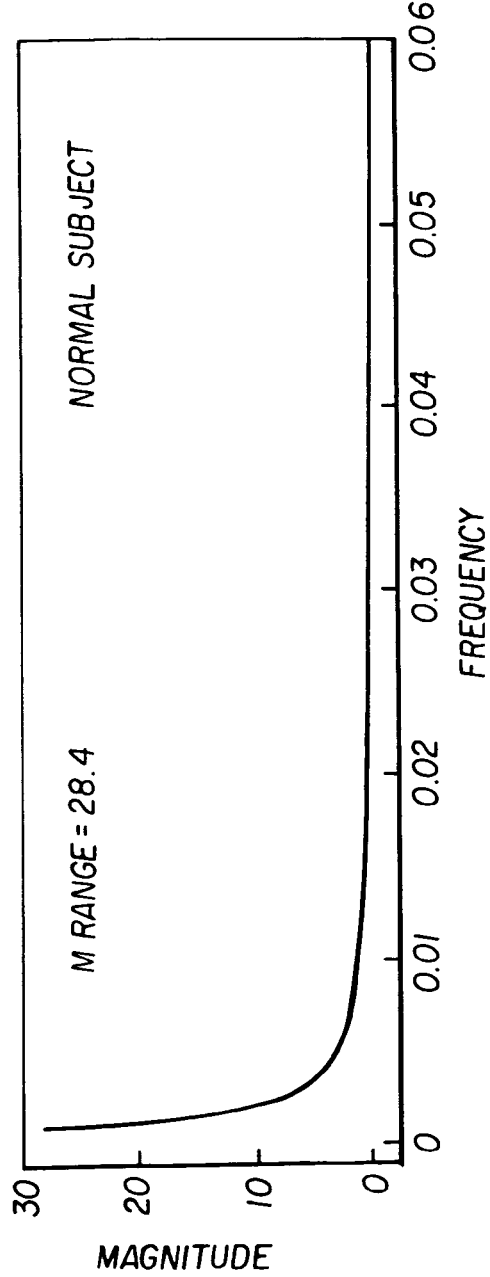
Figure 6:
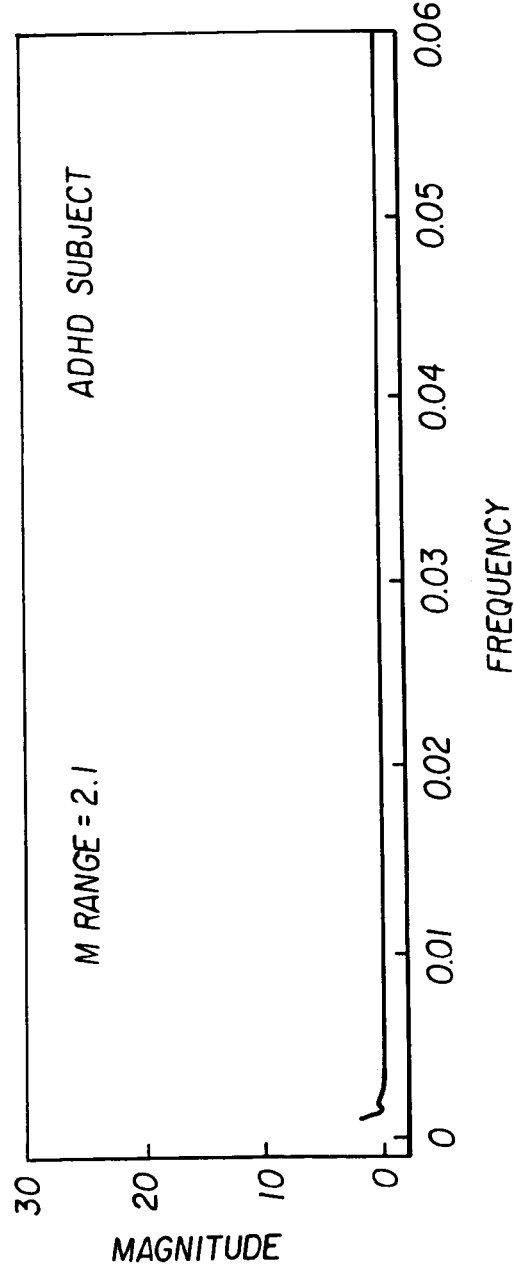
Figure 7:
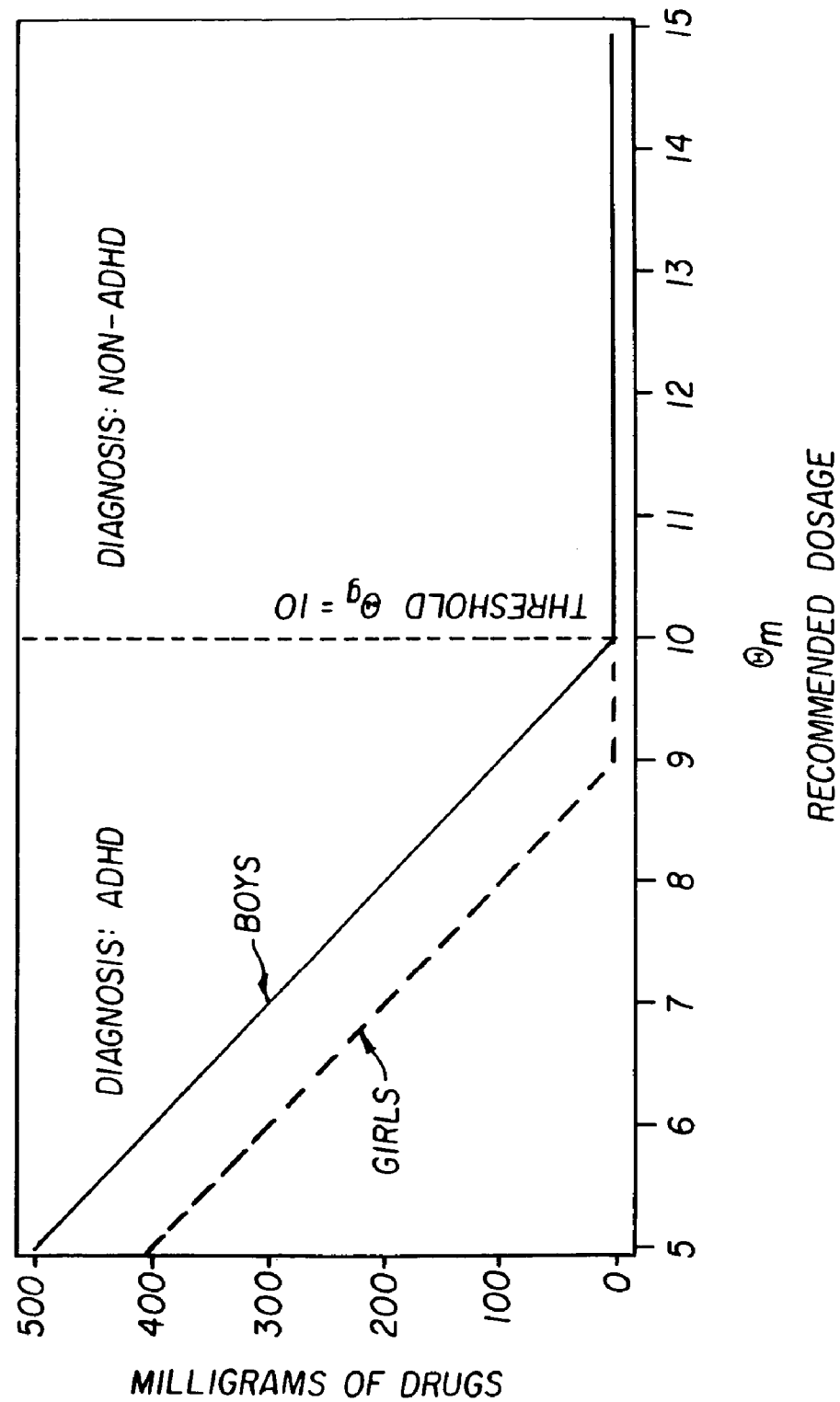
FIG. 7 is a diagram of an example of using the threshold $\theta_g$ and the patient's computed aggregation statistic $\Theta_m$ to diagnose the presence or absence of ADHD and determine the suggested drug dosage.

FIGS. 5 and 6 graphically illustrate the magnitude transform for the data corresponding with a subject with ADHD and normal subject. These spectral signatures of this first processing undergo dramatic changes essentially changing from a hyperbolic curve to a flat response. In FIG. 6, the magnitude range is substantially less than shown in FIG. 5, indicating ADHD manifestation.

Raw Data

The raw data $T_{k,l}(t)$ is the temperature taken from hand $_l$ at a fingertip 16 as shown in FIG. 1, during the 10-minute session. The sessions were taken over a period of weeks. Some subjects had as few as 2 sessions and some as many as 5 sessions k is used to represent the session.

Referring again to FIG. 3a:

Windows

The data for each session were divided into a series of windows (block 43) prior to performing the Fourier Transform operation. Call the window width w. In this analysis, the window width was 64 seconds and there were 10 windows spaced at 50-second intervals (the windows overlap) across the 600 sec baseline spanning the range of 100–500 sec, other values of w can be used. The window number in a session is referred to with the letter j. For each window a FFT algorithm calculates the Fourier Transform F(f). The Magnitude and Phase of this transform are defined as given above.

In block 46 the range of magnitude variation during a window is calculated using equation (1.2) below where $f_{max}$ and $f_{min}$ are the frequencies where the Magnitude is the greatest and the least respectively (note the dc component at frequency zero is excluded).

$$M_{range} = [M(f_{max}) - M(f_{min})] \quad (1.2)$$

In a further embodiment of this method, other statistics from a Fourier Transform, calculated from the quantities denoted above as $A(f_m)$, $B(f_m)$, $\theta(f_m)$, and $M(f_m)$ may be used. In addition to using Fourier Transforms, another embodiment may use statistics derived from a Wavelet transform of data or other filtering of the data (as in Strang, G. and Nguyen, T. (1996), *Wavelets and Filter Banks*, Wellesley-Cambridge Press, Wellesley, Mass.).

Aggregation of Samples

During this first processing, windowing the data for conversion to the frequency domain results in multiple first spectral signatures like those shown in FIGS. 5 and 6, which must be combined. MRange values for all windows are aggregated in block 47. There are z windows from each hand from each session. The first step is to choose an aggregation statistic, which can be the mean, median, variance, or other statistic, which is an aggregate of the computed $M_{range}$ values in each window for each session and each hand. Other statistics that may be used for aggregation include the standard deviation, range, interquartile distance, skewness, kurtosis, Winsorized mean and variance, and robust estimates of mean and variance. Equations below are given for aggregating the mean and the variance. The mean magnitude range for the left hand during session k is found from equation 2.0, where z is the number of windows in the session.

$$<M_{k,l}> = \frac{\sum_{j=1}^{z}[M(f_{\max})_j - M(f_{\min})_j]}{z} \quad (2.0)$$

And the corresponding variance is:

$$<Var_{k,l}> = \frac{\sum_{j=1}^{z}\{[M(f_{\max})_{j,l} - M(f_{\min})_{j,l}] - <M_{k,l}>\}^2}{z-1} \quad (2.1)$$

Combining these session means and variances over both hands and all the sessions s that a subject attended gives an aggregated mean μ and aggregated variance.

$$\mu = \frac{\sum_{k=1}^{s}\sum_{l=1}^{2}<M_{k,l}>}{2s} \quad (2.2)$$

$$<var> = \frac{\sum_{k=1}^{s}\sum_{l=1}^{2}var_{k,l}}{2s} \quad (2.3)$$

Further embodiments of this aggregation step of the first processing include using the data from only one hand—either the left hand, the right hand, or the dominant hand (and if the subject is ambidextrous, the dominant hand would be defined as the average of both hands). In addition, future embodiments may not require averaging of several sessions, but selecting only one session for use or using a weighted combination of each session's results.

Diagnostic Indicators

Referring again to FIG. 3a, the normalized group diagnostic threshold indicator $\theta_g$ was established previously from the aggregation statistics determined using data from a large group of subjects having similar demographic characteristics-block 49, and can vary based upon gender, age or weight. This group diagnostic threshold $\theta_g$ is calculated statistically from group temperature variability data using methods described in U.S. patent application Ser. No. 09/597,610, filed Jun. 20, 2000.

When the subject's measured aggregation statistic $\Theta_m$ (from equation 2.2 or 2.3) block 47 is less than the group threshold $\theta_g$- block 49, the test 48 indicates the subject has ADHD. When the measured aggregation $\Theta_m$ statistic is greater than the predetermined threshold $\theta_g$, the test indicates no manifestation of ADHD-block 50 and no medication is required-block 51. The same threshold $\theta_g$ may be used for all subjects or $\theta_g$ may have a value that is different for different groups based on gender or age.

Determination of Proper Dosage

Figure 3B:
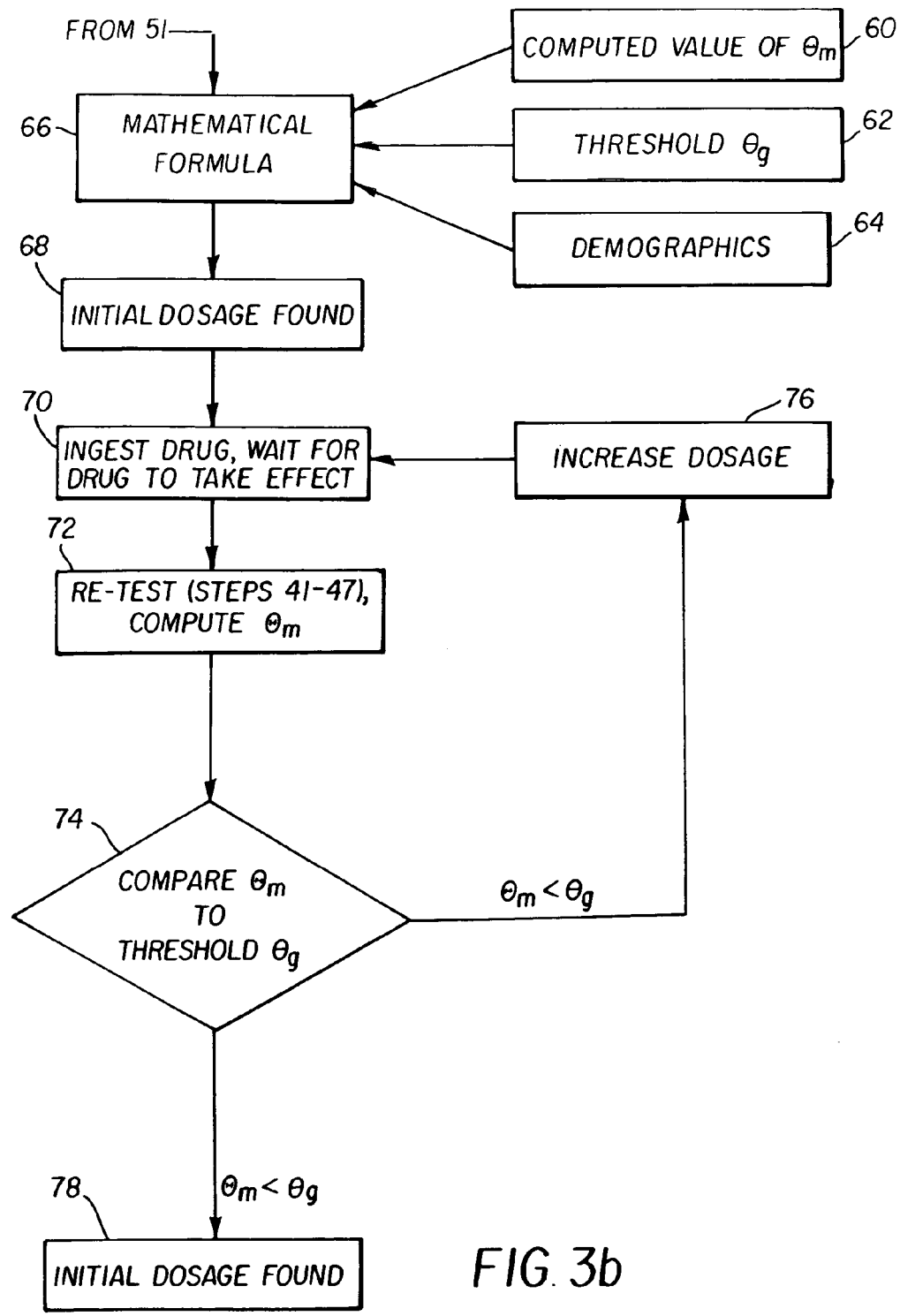

Now referring to FIG. 3b, based upon the computed value of the aggregation statistic $\Theta_m$-block 60 and the predetermined threshold value $\theta_g$-block 62, a mathematical formula-block 66 is used to compute the proper dosage-block 68 for subjects who are diagnosed as having ADHD. This mathematical formula may also include demographic information-block 64, including gender, age and weight. An example of such a mathematical formula is the following:

$$\text{Dosage} = 100_x(\theta_g - \Theta_m - 1) + 100_x \text{ gender}$$

where the dosage is in milligrams of a drug, and where gender is coded as 0 if the patient is female and 1 if the patient is male. For example, if $\theta_g=10$ and $\Theta_m=8$, and the patient is male, the example formula would call for a dosage of $100_x(10-8-1)+100_x1=200$ milligrams of the drug.

Medication Effectiveness Indicator

If the prescribed medication is effective in correcting the ADHD, then the measured physiologic diagnostic indicator $\Theta_m$ (as defined by equation 2.2 or 2.3) would be expected to come within the normal range and exceed $\theta_g$ during the time the patient is medicated Thus, to determine if the dosage is effective, the patient will be re-tested according to the following procedure as illustrated in FIG. 3b. The subject will take the prescribed dosage of the medication and then wait a certain period of time-block 70. The subject's peripheral temperature will be measured and $\Theta_m$ will be calculated-block 72. This time period can range from the minimum time it takes for the drug to become effective after ingestion, to the maximum length of time the drug is effective after ingestion, to the maximum length of time the drug is effective after ingestion. Ideally, the test will occur at a time period equal to the drug's half-life in the body (note that a profile of the drug's efficacy over time could be acquired by repeated, evenly spaced testing by the methods of the present invention, from the time of ingestion, to the cessation of effectiveness). Next, compare the newly computed $\Theta_m$ value to threshold $\theta_g$-block 74. If value of $\Theta_m$ moves to the non-ADHD region (above threshold $\theta_g$), it is concluded that the medication and dosage are appropriate-block 78. If value of $\Theta_m$ remains in the ADHD region (below threshold $\theta_g$), it is concluded that a larger dosage is needed block 76. The dosage can be increased according to best medical practices. This procedure blocks 70–78 can be repeated until appropriate medication and dosages are determined such that the patient's $\Theta_m$ value, when re-tested, is in the non-ADHD region (above threshold $\theta_g$).

Because a patient's physiology can change over time, the effective dosage may change over time as well. Thus, the patient needs to be monitored during the treatment period in accordance with the best medical practices. One such monitoring scheme, which should be followed during the entire time the patient is taking the drug, is to periodically re-test the patient. The interval between these periodic tests can for example, be one month to one year. The monitoring procedure involves repeating blocks 70–78. In one embodiment of the invention, the initial dosage found-block 78 could be replaced with an enhancement in which, if $\Theta_m$ exceeds $\theta_g$ by a large amount, the dosage is decreased, while if $\Theta_m$ exceeds $\theta_g$ by a small amount, then the proper dosage has been found Complementary Analysis Method In the preferred embodiment of the present invention, a second processing of the data allows the assessment of the bi-modality of the spectral energy of peripheral temperature variability where, for example, when ADHD is manifesting, the just described first processing determines a decrease of spectral energy below around 0.005 Hz, and the second processing next described determines an increase in bilaterally differential spectral energy 0.03 Hz. The opposite bi-modality should be seen with adequate medication.

Figure 8:
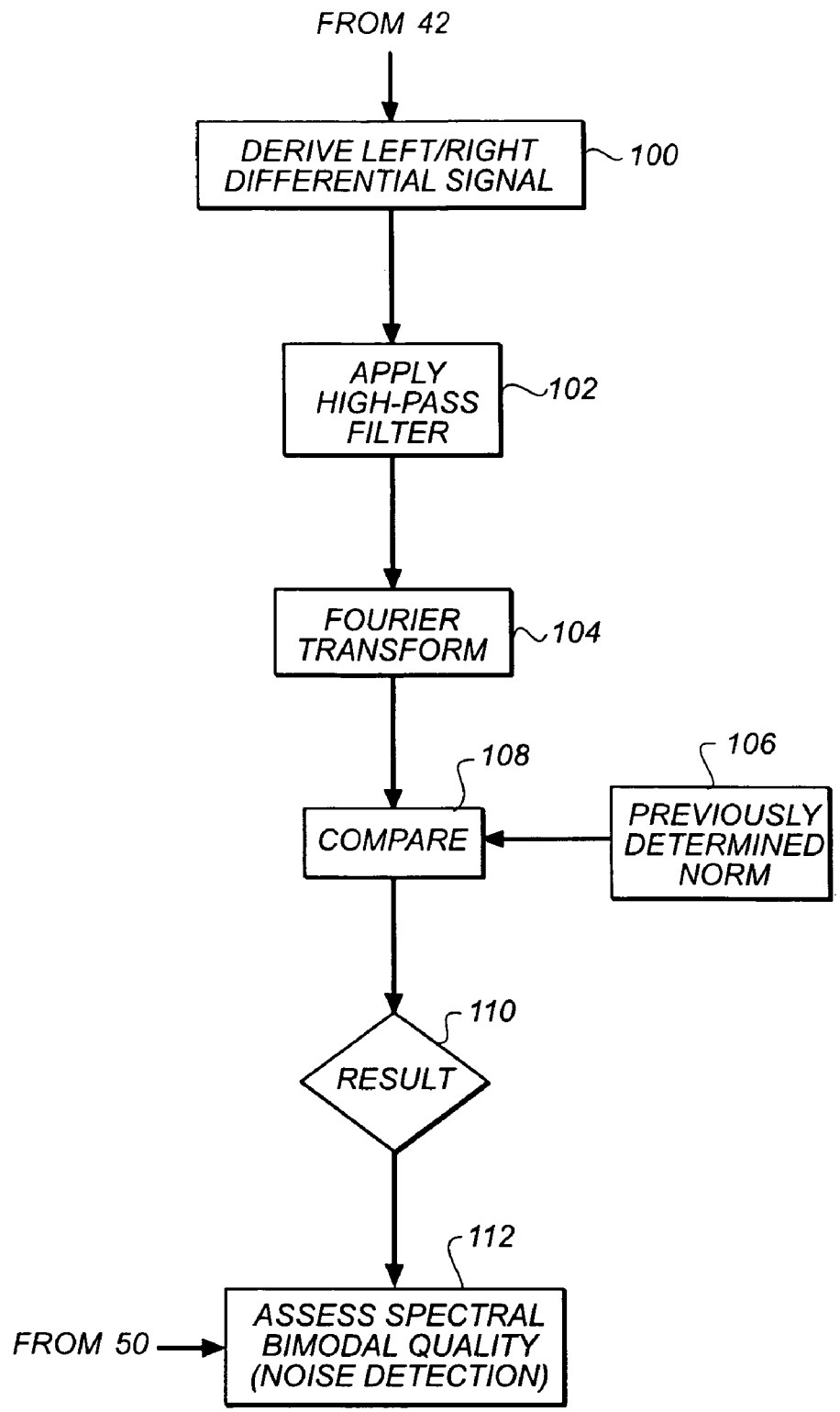
FIG. 8 is a block diagram of the second processing of the present invention.

Referring to FIG. 8, using the same sampled data from data storage 42 of FIG. 3a, the first step in the second processing is to subtract each data value of one hand from the temporal companion data of the other hand, producing a differential value 100 for each sample period. Next, a Butterworth High-pass Infinite Impulse Response Filter 102 is applied to the differential data, producing a roll-off characteristic, increasingly attenuating towards frequency zero. Removing the near-dc components in this way allows for greater discrimination of the area in the frequency domain of interest, empirically determined to center around 0.030 Hz., with the described filtering.

Figures 9, 10:
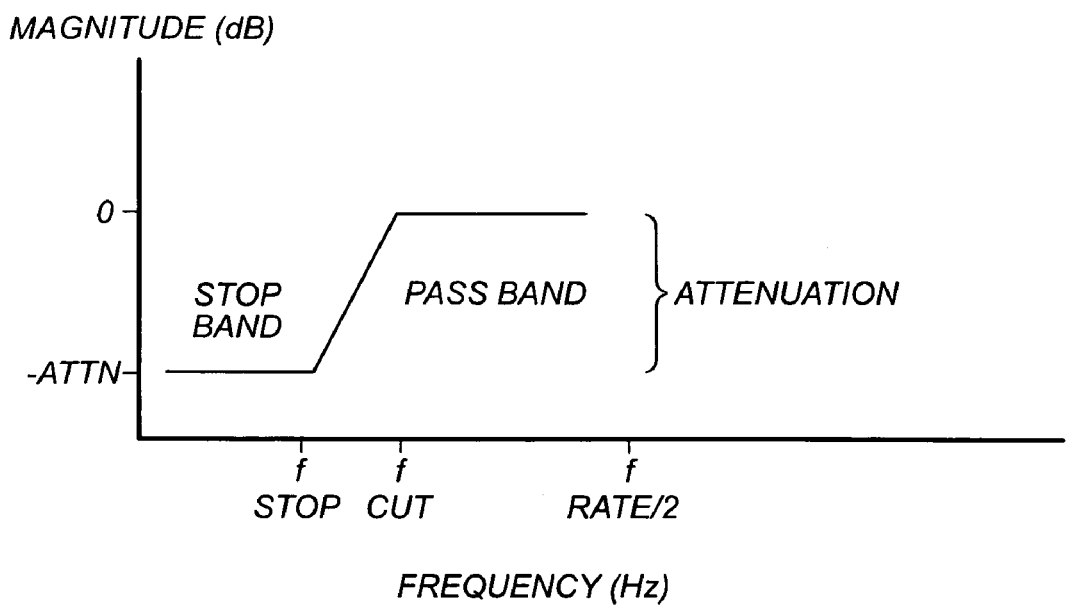
FIG. 9 is a table of the parameter values selected for the filter in accordance with the second processing of the present invention.
FIG. 10 is a graph of the filter parameters in accordance with the second processing of the present invention.
Figure 11:
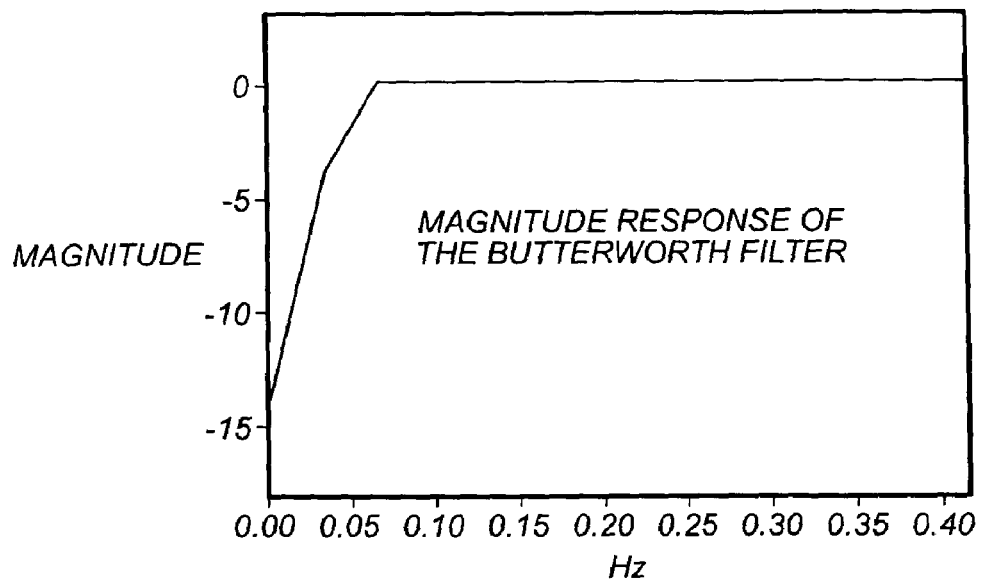
FIG. 11 is a plot of the spectral response of the filter of FIGS. 9 and 10.

As there may be differences in software to perform this transform, the application used is identified here as the DaDisp™ application by DSP Development Corporation. FIG. 9 is a table of the parameter values selected for the Butterworth Highpass IIR filter 102. FIG. 10 is a graph of the Butterworth Highpass IIR filter parameters. FIG. 11 is a plot of the spectral response for the Butterworth Highpass IIR filter of FIGS. 9 and 10.

Figure 12:
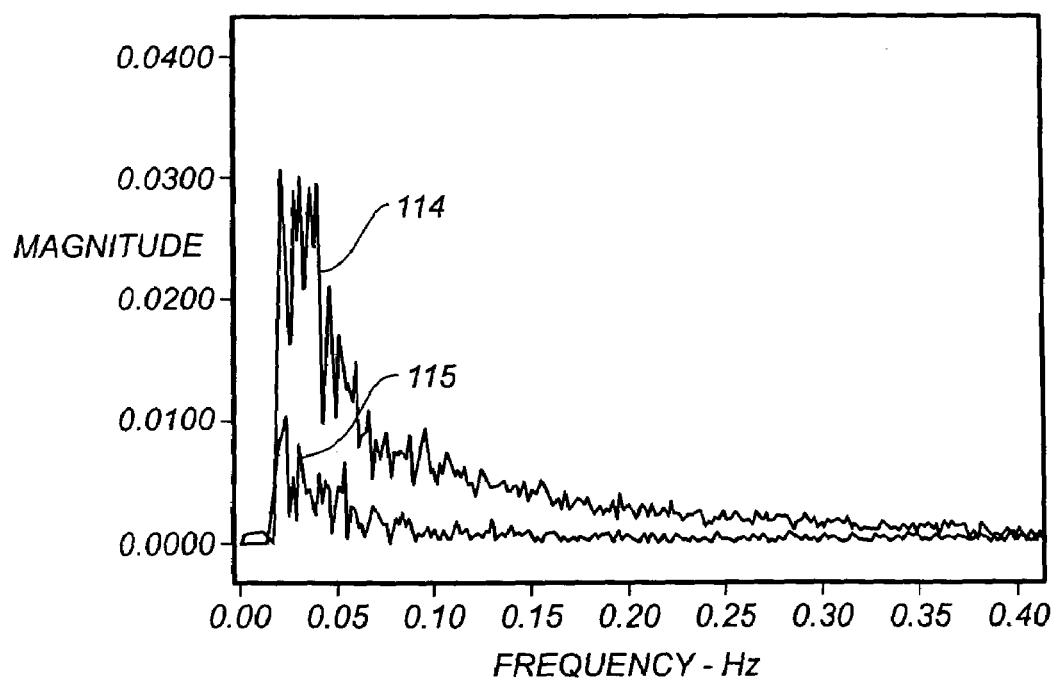
FIG. 12 is of sample of the second processing resultant spectral signature plots from two sessions, showing differing response.

The resultant high-passed differential data are then passed through a Fast Fourier Transform (also by DaDisp™) 104, to derive the spectral signature, which is then compared 108 against a pre-determined norm 106, generating result 110 of FIG. 8, in like manner to 47 through 50 of FIG. 3a for the first processing. FIG. 12 illustrates actual sample resultant plots of the spectral content of the filtered left/right hand temperature differential, showing a magnitude difference between an ADHD subject 114 and non-ADHD subject 115, of ratio 3 to 1. Here, as in the first processing, the effect of proper medication dosage for an ADHD subject is to make this processing spectral signature closer in magnitude to that seen with a non-ADHD subject. Test/adjust iteration for determination of propel dosage, as described in the first processing referencing FIG. 3b, includes the evaluation of this second processing result.

Thusly, similar to the analysis method of the first processing, the just described second processing provides a measurement means for medication effectiveness, that is, the magnitude of a final spectral signature. But with two differences: firstly, the portion of the spectrum of interest is centered around 0.03 Hz., and secondly, the magnitude of the spectral signature decreases in a proportion to the effectiveness of the medication.

It is therefore concluded here, considering the aforesaid determination, that very slow peripheral temperature variability is not simply suppressed in ADHD manifestation, but rather, moves upward in frequency, and becomes markedly bilaterally differential in nature.

The mechanism for this ADHD manifestation is thought to be the lessening of the slower, common control of the left and right peripheral temperatures by the autonomic nervous system, resulting in the control of temperature at said periphery being more localized and therefore less correlated to each other.

Multiplicity of Tests

A well known statistical principle is that the variability of the average of multiple tests is less than the variability of one test. Therefore, an advantage of effective, additional, concurrent testing, e.g. the combined analyses of the same session data, is increased accuracy.

Noise Detection

A key advantage of the present invention that combines the first processing and the just described second analysis processing is the ability to distinguish external noise from true physiological function. External noise will manifest as increased spectral content, which can occur anywhere in the spectrum, including within the regions of interest. It may be anywhere from broadband to very frequency-specific. Such noise is usually difficult to discern unless the specific frequency or bandwidth is known, which is not the case with such measurements.

The present invention provides a means for noise detection due to the nature of vasomotor activity. Peripheral temperatures are ultimately controlled in all cases, thereby producing the same total spectral energy on average. The present invention provides complimentary tests of this feature of physiology, that if the magnitude of energy is less in one spectral region, the case in the first processing when ADHD is manifesting, the magnitude of energy is greater in the other spectral region, the case in the second processing, The matched opposites of these results indicate that the subject is receiving adequate medication. This bi-modal spectral characteristic will not be seen with noise since it can only be additive. Noise in the data is thereby identifiable. This is accomplished at block 112 of FIG. 8, which inversely compares result block 50 of FIG. 3a to result 110 of FIG. 8. (Note that this does not mean that the noise can be removed; the test is invalidated. The course of action is re-testing and/or the removal of the source of noise at the testing site).

According to the present invention then, the now described fist and second processing result in the following possible test outcomes:

1) a various level of dosage change
2) dosage level adequate
3) there is noise in the data The invention has been described in detail with particular reference to certain preferred embodiments thereof, but it will be understood that further study could indicate refinements and optimizations, ad that such variations and modifications can be effected within the spirit and scope of the invention.

PARTS LIST

10 subject
12 chair
13 table
14 screen
16 fingertip
17 digit groove
18 temperature recording module
20 headphones
22 sensor
24 on/off switch
26 display
27 cable
28 temperature sensor module 29 cable
30 battery
32 external low voltage power supply port
34 groove
36 temperature sensor
41 temperature sampling circuit
42 data storage
43 window blocking
44 Fourier transform
45 magnitude calculation
46 Mrange calculation
47 aggregation block
48 threshold comparison block
49 previously determined threshold $\theta_g$ block
50 decision block
51 no medication required block 51
60 computed value of aggregation statistic $\Theta_m$
62 threshold value $\theta_g$
64 demographics
66 mathematical formula to determine initial dosage
68 initial dosage
70 ingest drug and wait
72 re-test step
74 compare new $\Theta_m$ to threshold $\theta_g$
76 increase dosage
78 proper dosage
100 differential derivation block
102 filter block
104 Fourier transform block
106 previously determined norm
108 comparison block
110 result
112 noise detection block
114 ADHD subject spectral plot
115 non-ADHD subject spectral plot
118 memory card slot
119 memory card

What is claimed is:

1. A method of adjusting a medication to treat ADHD comprising:

administering an initial dosage of a medication to an individual who has ADHD;

after waiting a period of time for the medication to take effect, conducting an analysis of the peripheral skin temperatures of said individual including the processes of sampling, differentiation, filtering, conversion to the frequency domain, and comparison to predetermined values; and based on said comparison:

(a) maintaining said dosage if said comparison is now not indicative of ADHD, or (b) increasing said dosage if said comparison is still indicative of ADHD.

2. The method of claim 1 wherein said period of time is a function of the medication's half-life in a human body.

* * * * *

UNITED STATES PATENT AND TRADEMARK OFFICE
CERTIFICATE OF CORRECTION

PATENT NO. : 7,037,260 B2
APPLICATION NO. : 10/832824
DATED : May 2, 2006
INVENTOR(S) : Keirsbilck et al.

It is certified that error appears in the above-identified patent and that said Letters Patent is hereby corrected as shown below:

Column 2,
    Line 2, replace "Monastra et al," with --Monastra et al.,--; and
    Line 17, replace "integrated" with --Integrated--; and
    Line 25, replace "U.S. Pat." with --11. U.S. Pat.--; and
    Line 26, replace "system and for managing" with --system for managing--; and
    Line 28, replace "U.S. Pat." with --12. U.S. Pat.--; and
    Line 43, replace "by American" with --by the American--.

Column 3,
    Line 19, replace "d, c," with --d.c.--; and
    Line 35, replace "adequate" with --adequate;--.

Column 4,
    Line 3, replace "is of sample," with --is a sample--; and
    Line 49, replace "photoplethismography" with --photoplethysmography--.

Column 5,
    Line 23, replace "a session The" with --a session. The--; and
    Line 29, replace "RS 232 cable" with --RS 232 cable--; and
    Line 48, replace "Fig. w" with --FIG. 2--; and
    Line 51, replace "provides 32 samples" with --provides 32 samples--.

Column 6,
    Line 34, replace "$_1$" with --1--; and
    Line 38, replace "sessions k" with --sessions. k--; and
    Line 62, replace "M ($f_m$)" with --M($f_m$)--.

UNITED STATES PATENT AND TRADEMARK OFFICE
CERTIFICATE OF CORRECTION

PATENT NO. : 7,037,260 B2
APPLICATION NO. : 10/832824
DATED : May 2, 2006
INVENTOR(S) : Keirsbilck et al.

It is certified that error appears in the above-identified patent and that said Letters Patent is hereby corrected as shown below:

Column 8,
    Line 1, replace "threshold $\theta_{g^-}$ block" with --threshold $\theta_g$-block--; and
    Lines 18-19, replace "Dosage=$100_x(\theta_g-\Theta_m-1)+100_x$gender" with
--$100 \times (\theta_g-\Theta_m-1)+100 \times$ gender--; and
    Line 24, replace "$100_x(10-8-1)+100_x 1=200$ milligrams" with
--$100 \times (10-8-1)+100 \times 1 = 200$ milligrams--; and
    Line 31, replace "medicated" with --medicated.--; and
    Lines 39-41, replace "to the maximum length of time the drug is effective after ingestion, to the maximum length of time the drug is effective after ingestion." with --to the maximum length of time the drug is effective after ingestion.--; and
    Line 52, replace "needed block" with --needed-block--; and
    Line 54, replace "procedure block" with --procedure-block--.

Column 9, Line 48, replace "propel" with --proper--.

Column 10,
    Line 30, replace "second processing," with --second processing--; and
    Line 41, replace "fist and second" with --first and second--; and
    Line 49, replace "ad" with --and--.

Signed and Sealed this

Twenty-ninth Day of September, 2009

David J. Kappos
*Director of the United States Patent and Trademark Office*